United States Patent
Thorson

(10) Patent No.: US 8,097,443 B2
(45) Date of Patent: Jan. 17, 2012

(54) NUCLEOTIDYLTRANSFERASES WITH ENHANCED NUCLEOTIDE TRIPHOSPHATE FLEXIBILITY

(75) Inventor: Jon S. Thorson, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 43 days.

(21) Appl. No.: 12/103,798

(22) Filed: Apr. 16, 2008

(65) Prior Publication Data

US 2008/0254509 A1    Oct. 16, 2008

Related U.S. Application Data

(60) Provisional application No. 60/912,009, filed on Apr. 16, 2007.

(51) Int. Cl.
*C12N 9/10* (2006.01)
*C12N 15/00* (2006.01)
*C12P 21/04* (2006.01)
*C12P 9/00* (2006.01)

(52) U.S. Cl. ...... 435/193; 435/69.1; 435/71.1; 435/440; 435/131

(58) Field of Classification Search ......... None
See application file for complete search history.

(56) References Cited

U.S. PATENT DOCUMENTS

| | | | |
|---|---|---|---|
| 4,683,195 A | 7/1987 | Mullis et al. | |
| 7,122,359 B2 * | 10/2006 | Thorson et al. | 435/193 |
| 2003/0055235 A1 * | 3/2003 | Thorson et al. | 536/23.2 |

FOREIGN PATENT DOCUMENTS

| WO | 0248331 | 6/2002 |
|---|---|---|
| WO | 2005056786 | 6/2005 |

OTHER PUBLICATIONS

Branden et al. Introduction to Protein Structure, Garland Publishing Inc., New York, p. 247, 1991.*
Jiang et al., J. Am. Chem. Soc., 122, 6803-6804. 2000.
Jiang et al., Angew. Chem., Int. Ed. 40, 1502-1505. 2001.
Jiang et al., ChemBioChem, 4, 443-446. 2003.
Fu et al., Nat. Biotechnol., 21, 1467-1469. 2003.
Ko et al., J. Org. Chem., 70, 1919-1921. 2005.
Griffith et al., Curr. Opin. Biotechnol., 16, 622-630. 2005.
Fu et al., Org. Lett., 7, 1513-1515. 2005.
Albermann et al., Org. Lett., 5, 933-936. 2003.
Bradford, Anal. Biochem., 72, 248-254. 1976.
Pace et al., Protein Sci., 4, 2411-2423. 1995.
Barton et al., Proc. Natl. Acad. Sci. U.S.A., 99, 13397-13402. 2002.
Zuccotti et al., J. of Mol. Biol., 313, 4, 831-843. 2001.
Lake et al., J. Biol. Chem., 275, 40211-40217. 2000.
Guex et al., Electrophoresis, 18, 2714-2723. 1997.
Humphrey et al., J. Mol. Graph., 14, 33-38, 27-38. 1996.
Persistence of Vision Pty. Ltd., http://www.povray.org, Jan. 6, 2009.
Lindquist et al., Eur. J. Biochem., 211, 763-770. 1993.
Bae et al., ChemBioChem, 6, 1963-1966. 2005.
Zhang et al., J. Biol. Chem., 280, 9698-9705. 2005.
Preiss et al., J. Biol. Chem., 239, 3119-3126. 1964.
Kimata et al., J. Biol. Chem., 241, 1099-1113. 1966.
Smoot et al., Eur. J. Biochem., 148, 83-87. 1985.
Amann et al., Carbohydr. Res., 335, 23-32. 2001.
Morrison, Methods Enzymol, 63, 257-294. 1979.
Schwarz, Cell. Mol. Life Sci., 62, 2792-2810. 2005.
PCT/US2008/060459—International Search Report, Nov. 20, 2008.
PCT/US2008/060459—Written Opinion of the International Searching Authority, Oct. 16, 2009.
Barton et al., Nature Structural Biology, New York, NY, 8, 6, 545-551. 2001.
Moretti et al., J. of Biol. Chem., 282, 23, 16942-16947. 2007.

* cited by examiner

*Primary Examiner* — Yong Pak
(74) *Attorney, Agent, or Firm* — Quarles & Brady LLP

(57) ABSTRACT

The present invention provides mutant RmlA enzymes possessing an increased purine/pyrimidine bias in nucleotide triphosphate substrate specificity as compared to a corresponding non-mutated RmlA enzyme. Such enzymes expand the types of substrates that can be used in enzymatic glycorandomization methods thereby increasing diversity of chemical libraries.

10 Claims, 7 Drawing Sheets

A

B

US 8,097,443 B2

SEQUENCE LISTING

<160> NUMBER OF SEQ ID NOS: 11

<210> SEQ ID NO 1
<211> LENGTH: 292
<212> TYPE: PRT
<213> ORGANISM: Salmonella enterica

<400> SEQUENCE: 1

```
Met Lys Thr Arg Lys Gly Ile Ile Leu Ala Gly Gly Ser Gly Thr Arg
1               5                   10                  15

Leu Tyr Pro Val Thr Met Ala Val Ser Lys Gln Leu Leu Pro Ile Tyr
            20                  25                  30

Asp Lys Pro Met Ile Tyr Tyr Pro Leu Ser Thr Leu Met Leu Ala Gly
```

```
                    35                  40                  45
Ile Arg Asp Ile Leu Ile Ile Ser Thr Pro Gln Asp Thr Pro Arg Phe
 50                  55                  60
Gln Gln Leu Leu Gly Asp Gly Ser Gln Trp Gly Leu Asn Leu Gln Tyr
 65                  70                  75                  80
Lys Val Gln Pro Ser Pro Asp Gly Leu Ala Gln Ala Phe Ile Ile Gly
                 85                  90                  95
Glu Glu Phe Ile Gly His Asp Asp Cys Ala Leu Val Leu Gly Asp Asn
                100                 105                 110
Ile Phe Tyr Gly His Asp Leu Pro Lys Leu Met Glu Ala Ala Val Asn
                115                 120                 125
Lys Glu Ser Gly Ala Thr Val Phe Ala Tyr His Val Asn Asp Pro Glu
130                 135                 140
Arg Tyr Gly Val Val Glu Phe Asp Gln Lys Gly Thr Ala Val Ser Leu
145                 150                 155                 160
Glu Glu Lys Pro Leu Gln Pro Lys Ser Asn Tyr Ala Val Thr Gly Leu
                165                 170                 175
Tyr Phe Tyr Asp Asn Ser Val Val Glu Met Ala Lys Asn Leu Lys Pro
                180                 185                 190
Ser Ala Arg Gly Glu Leu Glu Ile Thr Asp Ile Asn Arg Ile Tyr Met
                195                 200                 205
Glu Gln Gly Arg Leu Ser Val Ala Met Met Gly Arg Gly Tyr Ala Trp
                210                 215                 220
Leu Asp Thr Gly Thr His Gln Ser Leu Ile Glu Ala Ser Asn Phe Ile
225                 230                 235                 240
Ala Thr Ile Glu Glu Arg Gln Gly Leu Lys Val Ser Cys Pro Glu Glu
                245                 250                 255
Ile Ala Phe Arg Lys Asn Phe Ile Asn Ala Gln Gln Val Ile Glu Leu
                260                 265                 270
Ala Gly Pro Leu Ser Lys Asn Asp Tyr Gly Lys Tyr Leu Leu Lys Met
                275                 280                 285
Val Lys Gly Leu
    290

<210> SEQ ID NO 2
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 2
cttcaatata aagtagagcc aagcccggat gg                              32

<210> SEQ ID NO 3
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 3
ccatccgggc ttggctctac tttatattga ag                              32

<210> SEQ ID NO 4
<211> LENGTH: 32
<212> TYPE: DNA
<213> ORGANISM: ARTIFICIAL
<220> FEATURE:
```

<223> OTHER INFORMATION: PCR PRIMER

<400> SEQUENCE: 4
cttcaatata aagtagcccc aagcccggat gg          32

<210> SEQ ID NO 5
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 5
ccatccgggc ttggggctac tttatattga ag          32

<210> SEQ ID NO 6
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 6
cttcaatata aagtatcccc aagcccggat gg          32

<210> SEQ ID NO 7
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 7
ccatccgggc ttggggatac tttatattga ag          32

<210> SEQ ID NO 8
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 8
cttcaatata aagtagaccc aagcccggat gg          32

<210> SEQ ID NO 9
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 9
ccatccgggc ttggtctac tttatattga ag           32

<210> SEQ ID NO 10
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 10
cttcaatata aagtaaaccc aagcccggat gg          32

<210> SEQ ID NO 11

```
<211> LENGTH: 32
<212> TYPE: DNA
<213> ORGANISM: ARTIFICIAL
<220> FEATURE:
<223> OTHER INFORMATION: PCR PRIMER

<400> SEQUENCE: 11
ccatccgggc ttgggtttac tttatattga ag                                  32
```

NUCLEOTIDYLTRANSFERASES WITH ENHANCED NUCLEOTIDE TRIPHOSPHATE FLEXIBILITY

CROSS-REFERENCE TO RELATED APPLICATIONS

This application claims priority to U.S. Provisional Application No. 60/912,009, filed Apr. 16, 2007, which is incorporated herein by reference in its entirety.

STATEMENT REGARDING FEDERALLY SPONSORED RESEARCH

This invention was made with United States government support awarded by the following agencies: NIH AI052218. The United States government has certain rights in this invention.

FIELD OF THE INVENTION

This invention relates generally to the fields of enzymatic glycorandomization and the production of diverse chemical libraries. More particularly, the present invention is directed to nucleotidyltransferases possessing enhanced nucleotide triphosphate flexibility. Such enzymes broaden the number of sugar substrate families available for use in enzymatic glycorandomization.

BACKGROUND OF THE INVENTION

Carbohydrates are vital in nature, not only for energy metabolism, but also as structural scaffolds, recognition motifs, solubility aids, and functional modulators. Yet despite the vast structural and functional diversity of natural glycoconjugates, they are constructed via common biosynthetic themes. Specifically, sugars are attached to most proteins, lipids, carbohydrates, and small molecules by glycosyltransferases which, with few exceptions, use sugar nucleotides as the monosaccharide donors. These sugar nucleotides are constructed from sugar-1-phosphates and NTPs by sugar-1-phosphate nucleotidyltransferases, also referred to as sugar nucleotide pyrophosphorylases (E.C. 2.7.7.-), providing the precursors (usually ADP-, CDP-, GDP-, UDP- and dTDP-glucoses, as well as GDP-mannose, GDP-fucose, and UDP-N-acetylglucosamine) central to nearly all glycosylation-dependent processes.

Nucleotidyltransferases are prevalent in nature [there are currently ~14,000 known and putative nucleotidyltransferase sequences in GenBank], are often allosterically controlled, and generally proceed via ordered bi-bi mechanisms. For example, the forward reaction catalyzed by *Salmonella* glucose-1-phosphate thymidylyltransferase (RmlA), set forth herein as SEQ ID NO:1 (deposited as GenBank Accession No. CAA40117), proceeds via direct $S_N2$ attack upon the NTP α-phosphate by an α-D-sugar anomeric phosphate to provide the desired sugar nucleotide and pyrophosphate (FIG. 1). Nucleotidyltransferases from both prokaryotes and eukaryotes have reported flexibility toward variant sugar phosphates in vitro and the uniquely broad sugar-1-phosphate tolerance of RmlA has been exploited for the synthesis of diverse UDP- and dTDP-based sugar nucleotide libraries and enhanced via structure-based engineering. To date, more than 30 different sugar-1-phosphates have been reported as substrates for RmlA variants.

The corresponding pyrimidine-based sugar nucleotide libraries have served as the foundation for a process known as natural product glycorandomization (FIG. 1B)—an enzymatic strategy to exchange natural product sugars with diverse sugar arrays. To date this strategy has been applied toward the diversification of glycopeptide, coumarin and macrolide antibiotics, as well as anthelmintic avermectin and enediyne anticancer agents. Yet while there exist limited reports wherein sugar-1-phosphate guanylyl- or adenylyl-transferases displayed moderate sugar-1-phosphate flexibility, the lack of a general strategy to generate diverse purine-based sugar nucleotide libraries excludes the corresponding diversification of many natural products glycosylated by purine sugar nucleotide-dependent glycosyltransferases.

Recently, thermophilic uridylyl- and thymidylyl-transferases were revealed to utilize alternative nucleotides, including both ribo- and deoxyribo-variants of one or more purine nucleotides. However, no single enzyme has been reported to utilize all eight naturally occurring NTPs. As can be appreciated, a single "universal" nucleotidyltransferase is highly desirable and would greatly benefit the production of diverse chemical libraries enzymatic and, in particular, enzymatic glycorandomization methodology.

SUMMARY OF THE INVENTION

The present inventor's determination of RmlA nucleoside triphosphate specificity revealed this catalyst to utilize all eight naturally occurring NTPs, with varying levels of catalytic efficiency, even in the presence of non-native sugar-1-phosphates. The uniquely broad synthetic utility of RmlA was then enhanced by structure-based engineering to yield several mutant RmlA enzymes possessing an increased purine/pyrimidine bias in nucleoside triphosphate substrate specificity as compared to a corresponding non-mutated RmlA enzyme.

Accordingly, the invention provides in a first aspect an isolated RmlA nucleotidyltransferase comprising the amino acid sequence set forth in SEQ ID NO:1 having a mutation at position 83 from glutamine to glutamic acid, alanine, serine, aspartic acid, or asparagine. The resulting mutant RmlA nucleotidyltransferase exhibits an increased purine/pyrimidine bias in nucleoside triphosphate substrate specificity as compared to a corresponding non-mutated RmlA nucleotidyltransferase.

In a second aspect, the invention encompasses a method of providing a mutant RmlA nucleotidyltransferase with increased purine/pyrimidine bias in nucleoside triphosphate substrate specificity. Such method includes steps of: (a) mutating an isolated nucleic acid sequence encoding an RmlA nucleotidyltransferase having the amino acid sequence set forth in SEQ ID NO:1 to replace glutamine at position 83 with glutamic acid, alanine, serine, aspartic acid, or asparagine; (b) expressing the isolated nucleic acid in a host cell; and (c) isolating from the host cell a mutant RmlA nucleotidyltransferase that exhibits an increased purine/pyrimidine bias in nucleoside triphosphate substrate specificity as compared to a corresponding non-mutated RmlA nucleotidyltransferase.

In yet another aspect, the invention provides a method of providing a nucleotide-diphospho-sugar. Such a method includes steps of incubating a nucleoside triphosphate and a sugar-1-phosphate in the presence of an isolated mutant RmlA nucleotidyltransferase as described and claimed herein to enzymatically provide a nucleotide-diphospho-sugar.

Other objects, features and advantages of the present invention will become apparent after review of the specification, claims and drawings.

DETAILED DESCRIPTION OF THE INVENTION

Figure 1:
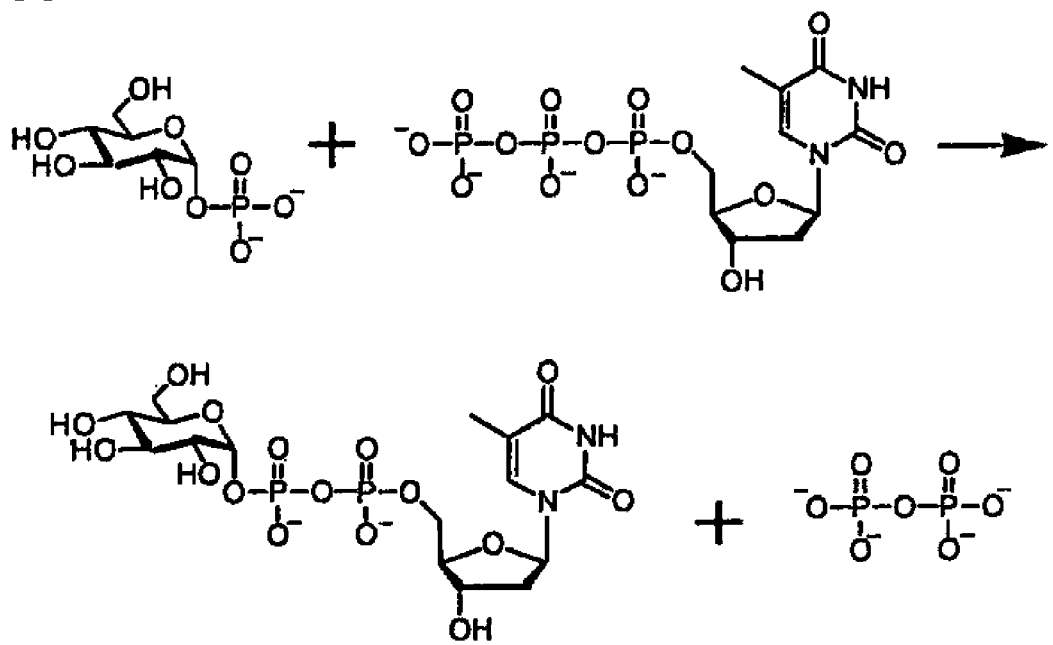
FIG. 1(A) illustrates the wt RmlA reaction.
FIG. 1(B) depicts an overview of glycorandomization. Natural or unnatural free sugars are enzymatically converted to nucleotide sugar donors through a two-step process catalyzed by a set of promiscuous anomeric kinases and sugar-1-phosphate nucleotidyltransferases, respectively. The inherent substrate flexibility of most natural product glycosyltransferases subsequently allow the ability to use unique sets of sugar nucleotides to generate libraries of differentially-glycosylated natural products. The sphere represents any given natural product and a key to this process is the ability of all participating enzymes to accommodate substrate diversity.
Figure 1:
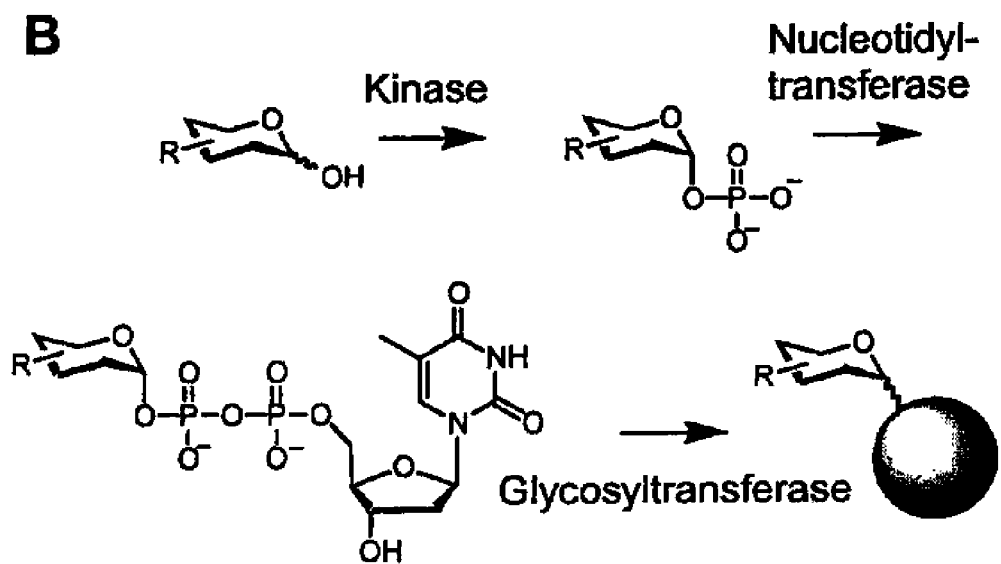

Before the present materials and methods are described, it is understood that this invention is not limited to the particular methodology, protocols, materials, and reagents described, as these may vary. The terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein, and the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The following abbreviations are used herein: NTP, nucleotide-5'-triphosphate; ATP, adenosine-5'-triphosphate; CTP, cytidine-5'-triphosphate; GTP, guanosine-5'-triphosphate; UTP, uridine-5'-triphosphate; dATP, 2'-deoxyadenosine-5'-triphosphate; dCTP, 2'-deoxycytidine-5'-triphosphate; dGTP, 2'-deoxyguanosine-5'-triphosphate; dTTP, 2'deoxythymidine-5'-triphosphate; NDP-sugar, nucleotide diphosphosugar; IPTG, isopropyl-β-D-thiogalactopyranoside; BSA, bovine serum albumin; wt, wild-type; SDS-PAGE, sodium dodecyl sulfate-polyacrylamide gel electrophoresis.

Nucleotidyltransferases are central to nearly all glycosylation-dependent processes and have been used extensively for the chemoenzymatic synthesis of sugar nucleotides. In this regard, the present invention is directed to engineering single universal nucleotidyltransferases and thereby providing new catalysts for the synthesis of novel NDP-sugars.

The manipulation of RmlA described herein is exemplary of the present invention. Specifically, the inventor's in-depth characterization of the NTP specificity of wild-type RmlA revealed wt RmlA to utilize all eight naturally occurring nucleoside triphosphates as substrates, with varying levels of catalytic efficiency, even in the presence of non-native sugar-1-phosphates. Based upon a composite nucleotidyltransferase purine-binding structural model, RmlA was subsequently engineered to provide mutants which displayed altered pyrimidine/purine biases by up to 3-orders of magnitude as measured by apparent $k_{cat}/K_M$. This approach therefore facilitates the production of diverse purine-based sugar nucleotide libraries and will not only enhance the prospects of natural product glycorandomization, but will also facilitate the production of novel reagents for glycobiology.

Accordingly, the invention provides in a first aspect an isolated RmlA nucleotidyltransferase comprising the amino acid sequence set forth in SEQ ID NO:1 having a mutation at position 83 from glutamine to glutamic acid, alanine, serine, aspartic acid, or asparagine. The resulting mutant RmlA nucleotidyltransferase exhibits an increased purine/pyrimidine bias in nucleoside triphosphate substrate specificity as compared to a corresponding non-mutated RmlA nucleotidyltransferase.

In a second aspect, the invention encompasses a method of providing a mutant RmlA nucleotidyltransferase with increased purine/pyrimidine bias in nucleoside triphosphate substrate specificity. Such method includes steps of: (a) mutating an isolated nucleic acid sequence encoding an RmlA nucleotidyltransferase having the amino acid sequence set forth in SEQ ID NO:1 to replace glutamine at position 83 with glutamic acid, alanine, serine, aspartic acid, or asparagine; (b) expressing the isolated nucleic acid in a host cell; and (c) isolating from the host cell a mutant RmlA nucleotidyltransferase that exhibits an increased purine/pyrimidine bias in nucleoside triphosphate substrate specificity as compared to a corresponding non-mutated RmlA nucleotidyltransferase.

In yet another aspect, the invention provides a method of providing a nucleotide-diphospho-sugar. Such a method includes steps of incubating a nucleoside triphosphate and a sugar-1-phosphate in the presence of an isolated mutant RmlA nucleotidyltransferase as described and claimed herein to enzymatically provide a nucleotide-diphospho-sugar.

In certain embodiments, the nucleoside triphosphate is a purine nucleoside triphosphate. Alternatively, the nucleoside triphosphate is a pyrimidine nucleoside triphosphate.

The nucleoside triphosphate may further be a deoxyribose-containing nucleoside triphosphate or, alternatively, a ribose-containing nucleoside triphosphate.

In preferred embodiments, the sugar-1-phosphate is a hexose-1-phosphate, more preferably selected from 6-amino-6-deoxyglucose, glucosamine, mannose, galactose, glucose, N-acetyl-glucosamine, 3-O-methyl-glucose, 6-deoxyglucose, 3-azido-3-deoxyglucose, or 4-azido-4-deoxyglucose.

It is certainly envisioned that the present invention provides methods utilizing a plurality of different nucleoside triphosphates and a plurality of different sugar-1-phosphates to enzymatically synthesize a plurality of different nucleotide-diphospho-sugars.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Materials and Methods

This example describes general materials and methods used to generate the data and results set forth in the following examples. Glucose-1-phosphate, mannose-1-phosphate, glucosamine-1-phosphate, N-acetyl-glucosamine-1-phosphate, galactose-1-phosphate, and NTPs were obtained from commercial sources (Sigma, St. Louis, Mo., USA; or Invitrogen, Carlsbad, Calif., USA) and used without further purification. The syntheses of 3-O-methyl-glucose-1-phosphate, 3-azido-3-deoxyglucose-1-phosphate, 4-azido-4-deoxyglucose-1-phosphate, 6-deoxyglucose-1-phosphate, and 6-amino-6-deoxyglucose-1-phosphate were previously described (Jiang et al. (2000) J. Am. Chem. Soc. 122, 6803-6804; Jiang et al. (2001) Angew. Chem., Int. Ed. 40, 1502-1505; Jiang et al. (2003) Chem Bio Chem 4, 443-446; and Fu et al. (2003) Nat. Biotechnol. 21, 1467-1469.) All other materials were reagent grade or better and purchased from Sigma-Aldrich (St. Louis, Mo., USA), or Fisher Scientific (Pittsburgh, Pa., USA). Analytical HPLC was performed using a Varian ProStar HPLC system (Varian Inc., Palo Alto, Calif., USA). Standard mass spectrometry utilized electrospray ionization and was performed using either an Agilent 100 HPLC-MSD mass spectrometer (Agilent Technologies, Palo Alto, Calif., USA) or a Micromass LCT mass spectrometer (Waters, Milford, Mass., USA).

Protein Expression and Purification—*Salmonella enterica typhimurium* LT2 wt RmlA and all engineered RmlA mutants were expressed as N-His$_6$ fusion proteins from pET28a-based expression plasmids (Novagen, Madison, Wis., USA) in *Escherichia coli* BL21 (DE3) in a manner similar to previous methods (Ko et al. (2005) J. Org. Chem. 70, 1919-1921; Griffith et al. (2005) Curr. Opin. Biotechnol. 16, 622-630; Fu et al. (2003) Nat. Biotechnol. 21, 1467-1469; Albermann et al. (2003) Org. Lett. 5, 933-936; Fu et al. (2005) Org. Lett. 7, 1513-15151). Specifically, an overnight starter culture of LB media containing 50 µg/mL kanamycin was directly inoculated from a glycerol stock of the desired expression strain. After growth overnight (37° C., 250 rpm), this culture was diluted 1:100 with 2×YT media (Sambrook, J., Fritsch, E. F., and Maniatis, T. (1989) Molecular Cloning: a library manual, 2nd Ed. Ed., Cold Spring Harbor Laboratory Press, New York) containing 50 µg/mL kanamycin, typically to a total volume of 1 L. The large-scale culture was subsequently grown (37° C., 250 rpm) to mid-log phase (OD$_{600}$~0.6), at which point IPTG was added to a 1 mM final concentration. Growth was continued for an additional 2-4 hours, the cells were collected by centrifugation (15 min, 5000×g), resuspended in 100 mL 50 mM sodium phosphate, pH 8.0 containing 300 mM NaCl and 20 mM imidazole on ice. The cells were lysed via incubation with 1 mg/mL lysozyme (~50,000 U/mg; Sigma, St. Louis, Mo., USA) for 30 min on ice followed by sonication (VirSonic 475; Virtis, Gardiner, N.Y.; 100 W, 4×30 s pulses, ~1 min between pulses) on ice. Protein was purified with Ni-NTA agarose resin or spin columns (Qiagen, Hilden, Germany) using manufacturer's protocols. As RmlA is not stable in the elution buffer (50 mM sodium phosphate, pH 8.0 containing 300 mM NaCl and 250 mM imidazole), the buffer was exchanged with 20 mM Tris-HCl, pH 7.5 containing 1 mM EDTA, 200 mM NaCl and 10% (v/v) glycerol via PD-10 gel filtration columns (GE Healthcare, Uppsala, Sweden). Purified RmlA was subsequently concentrated to >10 mg/mL, flash frozen in liquid nitrogen, and stored at −80° C. Protein concentrations were determined by Bradford assay (Bio-Rad, Hercules, Calif., USA) using BSA as a standard, and a molecular mass of 34.6 kDa (Bradford, M. M. (1976) Anal. Biochem. 72, 248-254). Spectrophotometric determination of protein concentration [calc. $\epsilon_{280}$=33350 cm$^{-1}$M$^{-1}$ (Pace et al. (1995) Protein Sci. 4, 2411-2423)] were consistent with the Bradford assay.

RmlA mutagenesis—RmlA mutants were generated with the Quikchange mutagenesis kit (Stratagene, La Jolla, Calif., USA) using the wt RmlA-pET28a parent expression plasmid as the template and the primers indicated in Table 1. Individual progeny plasmids were confirmed by DNA sequencing to carry the desired mutations. Driven by these mutant plasmids, the corresponding RmlA variants were subsequently expressed and purified as described above.

TABLE 1

Primers used in site-directed mutagenesis

Sequence (5' → 3')

| | | | |
|---|---|---|---|
| Q83E | for | CTTCAATATAAAGTA<u>GAG</u>CCAAGCCCGGATGG | (SEQ ID NO: 2) |
| | rev | CCATCCGGGCTTGG<u>CTC</u>TACTTTATATTGAAG | (SEQ ID NO: 3) |
| Q83A | for | CTTCAATATAAAGTA<u>GCC</u>CCAAGCCCGGATGG | (SEQ ID NO: 4) |
| | rev | CCATCCGGGCTTGG<u>GGC</u>TACTTTATATTGAAG | (SEQ ID NO: 5) |
| Q83S | for | CTTCAATATAAAGTA<u>TCC</u>CCAAGCCCGGATGG | (SEQ ID NO: 6) |
| | rev | CCATCCGGGCTTGG<u>GGA</u>TACTTTATATTGAAG | (SEQ ID NO: 7) |
| Q83D | for | CTTCAATATAAAGTA<u>GAC</u>CCAAGCCCGGATGG | (SEQ ID NO: 8) |
| | rev | CCATCCGGGCTTGG<u>GTC</u>TACTTTATATTGAAG | (SEQ ID NO: 9) |
| Q83N | for | CTTCAATATAAAGTA<u>AAC</u>CCAAGCCCGGATGG | (SEQ ID NO: 10) |
| | rev | CCATCCGGGCTTGG<u>GTT</u>TACTTTATATTGAAG | (SEQ ID NO: 11) |

Enzymatic Reactions—The enzyme assay was accomplished via slight modification of previously reported methods (Jiang et al. (2000) J. Am. Chem. Soc. 122, 6803-6804; Jiang et al. (2001) Angew. Chem., Int. Ed. 40, 1502-1505; Jiang et al. (2003) Chem Bio Chem 4, 443-446; Barton et al. (2002) Proc. Natl. Acad. Sci. U.S.A. 99, 13397-13402). In a typical reaction, sugar-1-phosphate (10 mM final) and enzyme (0.01-50 μM) were mixed with NTP (0.01-40 mM) in the presence of $MgCl_2$ ([NTP]+5 mM) and 10 U/mL inorganic pyrophosphatase (Sigma, St. Louis, Mo., USA) in 100 mM Tris HCl, pH 8.0 (20 μL final volume). Typical reactions were analyzed after 10 min at 37° C. and reaction times were extended for some slow reacting sugar/NTP combinations. Reactions were stopped by the addition of 80 μL prewarmed HPLC buffer and heat inactivation (95° C., 5 min). The amount of enzyme used and the incubation time was adjusted so that the reactions never proceeded to more than 10% turnover for kinetics, or 30% for activity assays. Equivalent reactions with heat denatured enzyme displayed no product formation as determined by HPLC.

Product Characterization—Reactions were analyzed via analytical HPLC (Supelcosil LC18-T; Supelco, Bellefonte, Pa.; 5 μm, 250×3 mm, 40 mM phosphoric acid, pH 6.5 with triethylamine, with a gradient of 0-10% MeOH over 20 min, 0.8 mL/min, $A_{254}$). Due to earlier elution, a 5 min 0% MeOH isocratic hold was performed prior to starting the gradient for CTP-containing reactions. For nucleotide sugar products with commercially available standards, HPLC peak identity was confirmed by co-elution. The retention times for sugar-nucleotide product peaks under the above HPLC program are listed in Table 2.

TABLE 2

Retention times for Sugar Nucleotides (in minutes)[a]

| | $CTP^b$ | dCTP | UTP | GTP | dTTP | dGTP | ATP | dATP |
|---|---|---|---|---|---|---|---|---|
| 6-amino-6-deoxyglucose | 3.1 | 4.6 | 4.1 | 6.7 | 10.6 | 11.8 | 11.9 | 17.0 |
| Glucosamine | 3.5 | 5.0 | 4.9 | 7.8 | 11.6 | 12.5 | 13.0 | 17.6 |
| Mannose | 5.2 | 7.1 | 7.2 | 10.2 | 14.0 | 15.2 | 15.7 | 20.2 |
| Galactose | 5.7 | 7.9 | 7.5 | 10.8 | 14.6 | 15.6 | 16.4 | 20.9 |
| Glucose | 6.2 | 8.4 | 8.2 | 11.2 | 16.0 | 15.8 | 16.4 | 20.8 |
| N-acetyl-glucosamine | 7.1 | 9.0 | 9.0 | 12.2 | 14.0 | 16.6 | 17.6 | 21.1 |
| 3-O-methyl-glucose | 9.6 | 10.9 | 10.5 | 13.4 | 17.7 | 18.3 | 19.1 | 21.2 |
| 6-deoxyglucose | 10.6 | 11.3 | 11.2 | 13.8 | 17.8 | 18.3 | 19.3 | 23.2 |
| 3-azido-3-deoxyglucose | 19.3 | 14.8 | 15.0 | 20.3 | 22.1 | 22.6 | 22.3 | 27.2 |
| 4-azido-4-deoxyglucose | 15.3 | 15.0 | 15.4 | 17.7 | 21.8 | 23.2 | 22.7 | 29.0 |

[a]Supelcosil LC18-T (Supelco, Bellefonte, PA, USA), 5 μM, 250 × 3 mm, 40 mM phosphoric acid, pH 6.5 with triethylamine, with a gradient of 0-10% MeOH over 20 min, 0.8 mL/min, $A_{254}$.
[b]with an additional 5 min isocratic hold at 0% MeOH prior to the start of the gradient.

Table 3 depicts the identities of representative new reaction products were confirmed by mass spectrometry.

TABLE 3

MS characterization for selected sugar nucleotides

| | Expected [M-H]$^-$ | Observed [M-H]$^-$ |
|---|---|---|
| ADP-Glucose | 588.1 | 588.1 |
| CDP-Glucose | 564.1 | 564.1 |
| GDP-Glucose | 604.1 | 604.1 |
| UDP-Glucose | 565.0 | 565.0 |
| dADP-Glucose | 572.1 | 572.1 |
| dCDP-Glucose | 548.1 | 548.1 |
| dGDP-Glucose | 588.1 | 588.1 |
| dTDP-Glucose | 563.1 | 563.1 |
| ADP Glucosamine | 587.1 | 587.2 |
| dADP-6-amino-6-deoxyglucose | 571.1 | 571.2 |
| CDP-6-deoxyglucose | 548.1 | 548.1 |

TABLE 3-continued

MS characterization for selected sugar nucleotides

|  | Expected [M-H]⁻ | Observed [M-H]⁻ |
|---|---|---|
| dCDP-4-azido-4-deoxyglucose | 573.1 | 573.2 |

Kinetic Measurements—Pseudo first order kinetics were obtained by fixing glucose-1-phosphate at a saturating concentration of 10 mM (Barton et al. (2001) Nat Struct Biol 8, 545-551), and titrating NTPs. At least eight different concentrations in the range of $\frac{1}{4} \times K_M$ to $4 \times K_M$ (0.09-20 mM for dTTP, 0.2-40 mM for others) were assayed in triplicate. Reaction rates were confirmed to be linear over twice the incubation time. Activities were corrected for time and enzyme concentrations, and the kinetic curves were fit to the Michaelis-Menton equation using SigmaPlot with the Enzyme Kinetics module (SPSS, Chicago, Ill., USA).

Structural Models of Active-Site Mutants—Atomic coordinates of enzyme structures were obtained from the RSCB protein databank [RmlA with dTTP: 1IIM and RmlA with UDP-Glc: 1IIN (Barton et al. (2001) Nat Struct Biol 8, 545-551); MobA with GTP: 1FRW (Lake et al. (2000) J. Biol. Chem. 275, 40211-40217)]. Point mutations were simulated by the mutation function of Swiss-PdbViewer (Guex et al. (1997) Electrophoresis 18, 2714-2723). Models of non-crystallographic ligands were created by manual overlay of nucleotide bases so that they were in the same plane as that of the crystallographic base. Mutant side chain positions were selected from the rotamer set provided, and no additional energy minimization was performed on the structures. Figures were generated with VMD (Humphrey et al. (1996) J. Mol. Graph. 14, 33-38, 27-38) and rendered with POV-Ray ((2004) Persistence of Vision Raytracer (Version 3.6), Persistence of Vision Pty. Ltd., http://www.povray.org/).

Example 2

Protein Expression and Purification

Figure 4:
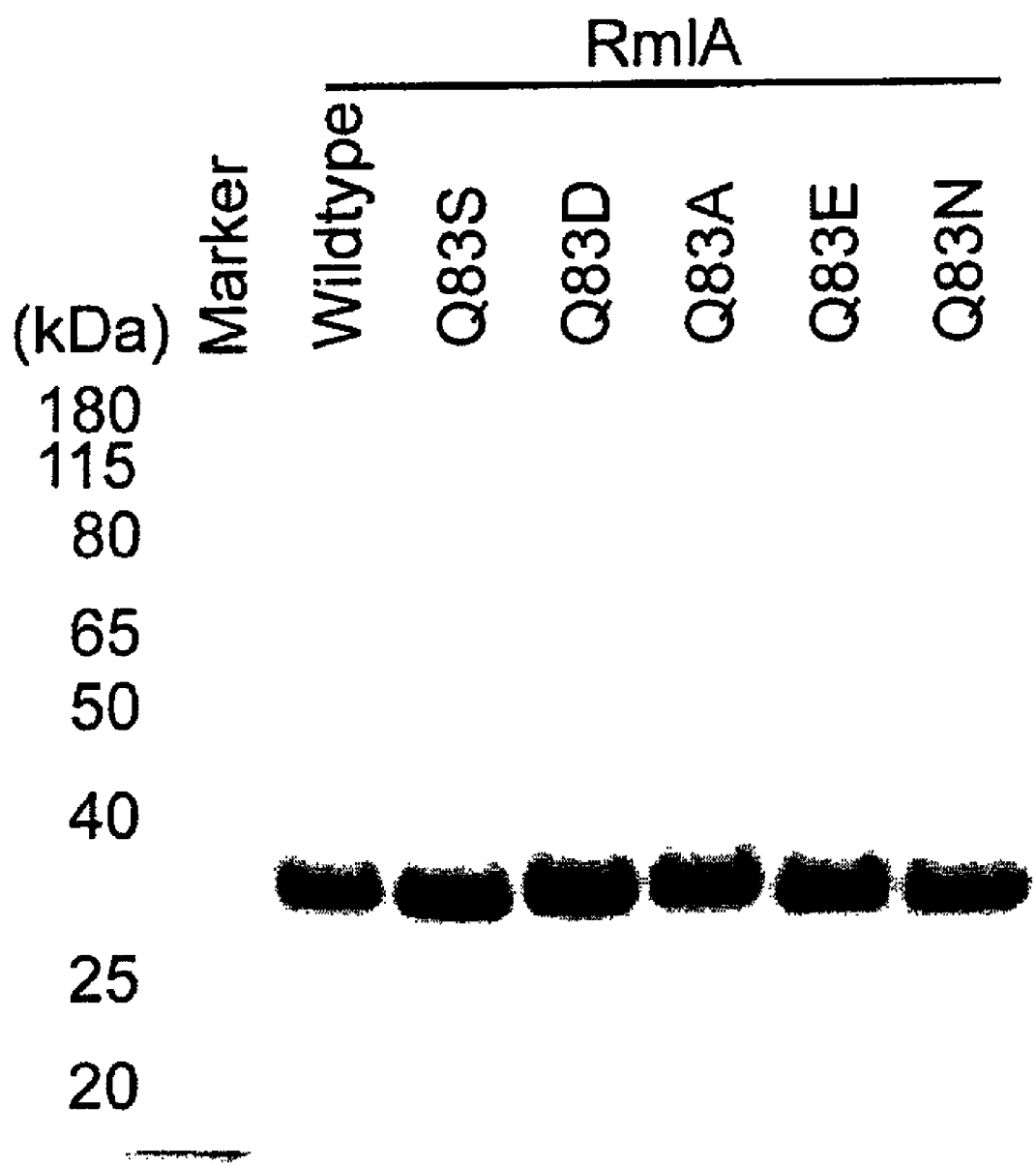
FIG. 4 depicts a Coomassie blue stained SDS-PAGE, showing purity of enzyme preparations after Ni-NTA column purification. The expected size of the $His_6$-RmlA fusion is 34.6 kDa.
Figure 5:
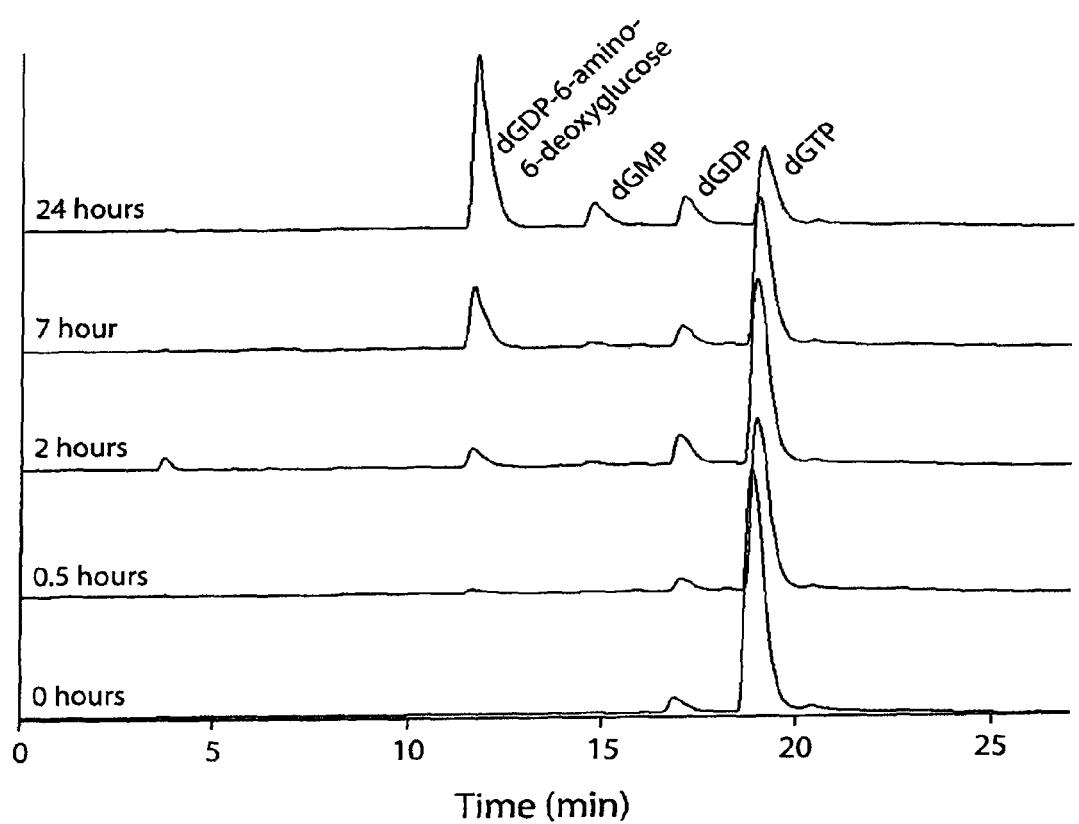
FIG. 5 illustrates representative chemoenzymatic synthesis of GDP-6-amino-6-deoxyglucose. Assay conditions: 50 µM wt RmlA, 5 mM dGTP, 10 mM 6-amino-6-deoxyglucose-1-phosphate, 100 mM Tris-HCl pH 8.0, 10 mM $MgCl_2$, and 10 U/mL inorganic pyrophosphatase at 37° C. At the time points indicated, aliquots were removed and analyzed by C18 reverse phase HPLC in a triethylamine phosphate buffer/methanol system. Although minimal conversion was observed at 30 minutes, incubation at 37° C. for 24 hours revealed >50% conversion to the desired product with minimal formation of side products.

The wild-type and mutant enzymes were expressed in soluble form at high levels (10-100 mg per liter of culture), and were purified to greater than 95% purity, as estimated by Coomassie stained SDS-PAGE, shown in FIG. 4. No significant differences in yield were noticed between the expression of wt RmlA and any of the RmlA mutants described herein.

Example 3

NTP Specificity of Wild-Type RmlA

Previous RmlA studies indicated a preference for the pyrimidine nucleoside triphosphates dTTP and, to a lesser extent, UTP using standard assay conditions (Barton et al. (2001) Nat Struct Biol 8, 545-551; Jiang et al. (2000) J. Am. Chem. Soc. 122, 6803-6804; Jiang et al. (2001) Angew. Chem., Int. Ed. 40, 1502-1505; Jiang et al. (2003) Chem Bio Chem 4, 443-446; Barton et al. (2002) Proc. Natl. Acad. Sci. U.S.A. 99, 13397-13402; Lindquist et al. (1993) Eur. J. Biochem. 211, 763-770). Recent work on thermophilic uridylyl- and thymidylyltransferases (*Thermus caldophilus* UDP-sugar pyrophosphorylase, or Usp, and *Sulfolobus tokodaii* ST0452, respectively) revealed the conversion of alternative nucleotides, including both ribo- and deoxyribo-variants of one or more purine nucleotides (Bae et al. (2005) Chem Bio Chem 6, 1963-1966; Zhang et al. (2005) J. Biol. Chem. 280, 9698-9705). Specifically, Usp was found to turn over glucose-1-phosphate with UTP, ATP, GTP, CTP, and dTTP. Alternatively, while ST0452 could not utilize ATP, CTP, or GTP, the enzyme showed good activity with UTP and the four deoxynucleoside triphosphates dATP, dTTP, dGTP ad dCTP. Given the high degree of amino acid similarity between Usp or ST0452 to RmlA (44% and 36%, respectively), these pioneering studies prompted a reevaluation of the RmlA purine nucleotide specificity.

Pseudo first-order Michaelis-Menton kinetic analysis revealed RmlA to turn over all eight 'natural' NTPs in the presence of glucose-1-phosphate (Table 4, below), albeit with appreciably reduced activity (~15-560-fold reduction in the apparent $k_{cat}$) in comparison to dTTP. The apparent $K_M$ for variant NTPs, including UTP, was also notably higher (~13-50-fold) than that for dTTP. This cumulative analysis translates to a drastic reduction in the apparent RmlA specificity constants ($k_{cat}/K_M$) for variant NTPs ranging from ~12-fold (UTP) to >15,000-fold (ATP) and is noteworthy for a number of reasons.

TABLE 4

Pseudo first order kinetic constants for RmlA[a]

|  |  | $k_{cat}^{app}$ (min⁻¹) | $K_M^{app}$ (mM) | $k_{cat}/K_M^{app}$ (min⁻¹ · mM) |
|---|---|---|---|---|
| Wild-type | dTTP | 1850 ± 40 | 0.29 ± 0.04 | 6300 ± 700 |
|  | UTP | 2460 ± 130 | 4.6 ± 0.7 | 530 ± 60 |
|  | dATP | 113 ± 5 | 7.8 ± 0.9 | 14.5 ± 1.1 |
|  | dCTP | 73 ± 3 | 10.5 ± 1.1 | 7.0 ± 0.4 |
|  | dGTP | 127 ± 5 | 3.7 ± 0.5 | 34 ± 4 |
|  | ATP | 3.32 ± 0.09 | 9.0 ± 0.6 | 0.39 ± 0.02 |
|  | CTP | 5.9 ± 0.2 | 13.7 ± 1.1 | 0.43 ± 0.02 |
|  | GTP | 8.4 ± 0.2 | 8.5 ± 0.6 | 0.99 ± 0.04 |
| Q83D | dTTP | 217 ± 14 | 6.2 ± 1.2 | 35 ± 5 |
|  | dGTP | 300 ± 20 | 11.5 ± 1.8 | 26 ± 2 |
|  | GTP | 12.8 ± 0.9 | 1.3 ± 0.4 | 10 ± 3 |
| Q83S | dTTP | 380 ± 30 | 2.4 ± 0.6 | 160 ± 30 |
|  | dATP | 320 ± 20 | 1.1 ± 0.3 | 280 ± 50 |
|  | ATP | 28.8 ± 1.4 | 3.4 ± 0.6 | 8.3 ± 1.1 |

[a]with 10 mM glucose-1-phosphate, 0.05-25 μM enzyme, [NTP] + 5 mM MgCl₂, 10 U/mL inorganic pyrophosphatase, in 100 mM Tris-HCl pH 8.0 at 37° C.

First, although RmlA has been used for the efficient synthesis of a variety of 'unnatural' UDP-sugars, the inventor identified the dTTP bias of RmlA to be dictated by $K_M$. Second, the present data highlights the apparent $K_M$s of all alternative 'natural' NTPs to increase ~10-fold while the large differences in the apparent $k_{cat}$s bias RmlA toward dTTP and UTP. Third, a comparison between the determined kinetic parameters for deoxyribose-containing nucleotides (dTTP, dATP, dCTP and dGTP) and ribose-containing nucleotides (UTP, ATP, CTP and GTP, respectively) suggests the ribose 2'-hydroxyl to contribute ~10-fold to the overall RmlA apparent nucleotide specificity ($k_{cat}/K_M$). This is consistent with previously reported influences of 2'hydroxylation upon nucleotidyltransferase activity (Preiss et al. (1964) J. Biol. Chem. 239, 3119-3126; Kimata et al. (1966) J. Biol. Chem. 241, 1099-1113; Smoot et al. (1985) Eur. J. Biochem. 148, 83-87). Finally, it should be noted that due to the high apparent $K_M$s for alternative nucleotides, preliminary assays were unsuccessful until the level of $Mg^{2+}$ was adjusted as per Morrison (Morrison, J. F. (1979) Methods Enzymol. 63, 257-294), lending support to the theory that the true nucleotidyltransferase substrate is a $Mg^{2+}$-NTP complex (Amann et al. (2001) Carbohydr. Res. 335, 23-32).

Example 4

Sugar-1-Phosphate Specificity with Variant NTPs

Figure 2:
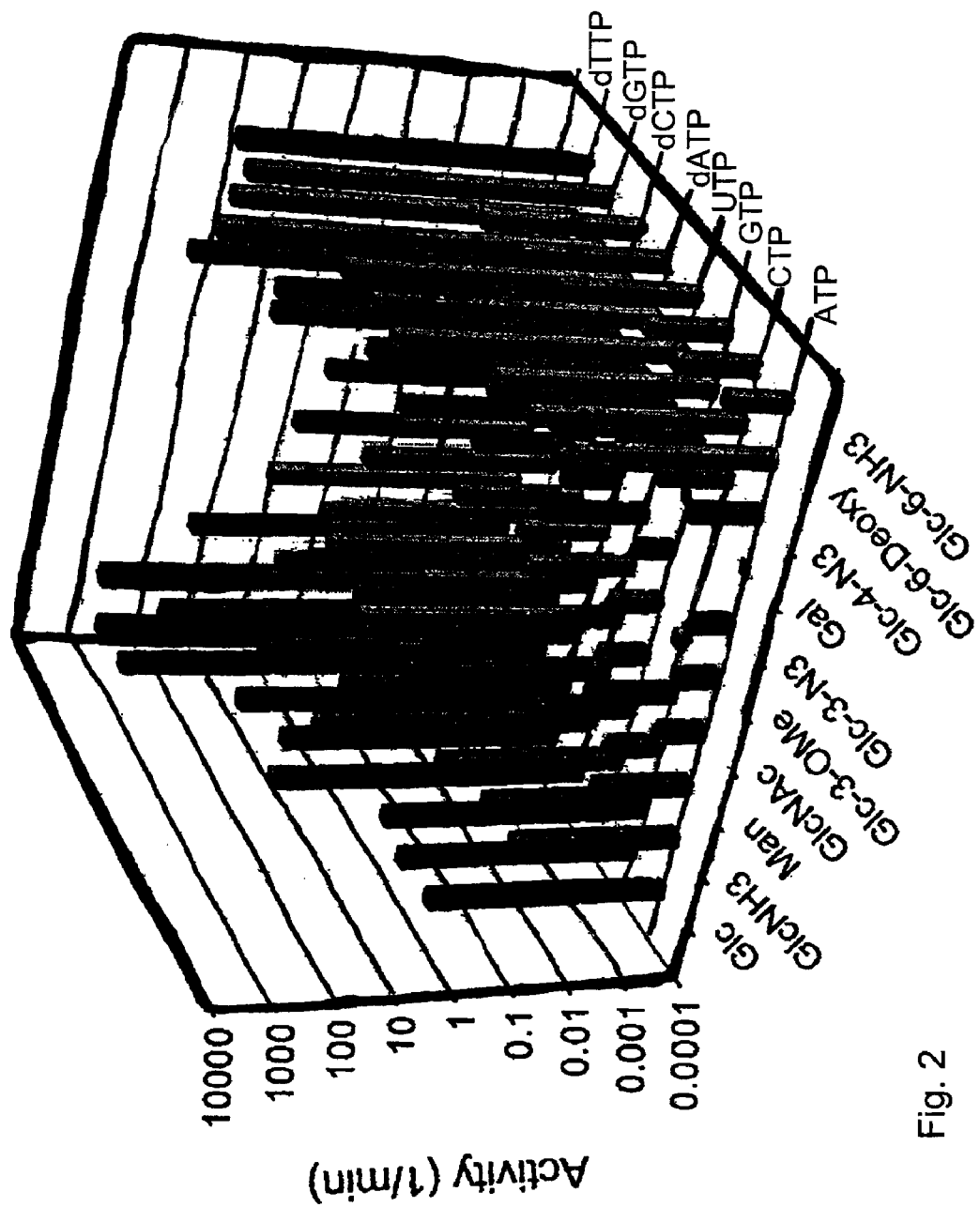
FIG. 2 shows specific activity of the wild-type RmlA toward variant sugar/nucleotide combinations, at 5 mM NTP and 10 mM sugar-1-phosphate. Substrates were reacted with 0.05-50 µM enzyme in 100 mM Tris-HCl pH 8.0, 10 mM $MgCl_2$, and 10 U/mL inorganic pyrophosphatase at 37° C. for 10-1000 minutes and substrates/products resolved via C18 reverse phase HPLC in a triethylamine phosphate buffer/methanol system. Activities are plotted on a log scale to accommodate the large range of values.

In light of the newly discovered ability of RmlA to employ variant NTPs, the specific activity of RmlA in the presence of a variety of 'unnatural' sugar phosphate/NTP combinations was assessed. Turnover was observed with nearly all sugar phosphate/NTP combinations examined, albeit with reductions in overall efficiencies up to $10^7$-fold (FIG. 2). Consistent with previous studies, wt RmlA was found to be least tolerant of sugar C3/C4-substitutions in the presence of alternative NTPs and alteration of both the NTP and sugar-1-phosphate typically exceeded an additive effect—previously noted as 'adversely cooperative' (Jiang et al. (2000) J. Am. Chem. Soc. 122, 6803-6804). Yet despite the adverse cooperativity and large reductions in catalytic efficiency, the clean production of this new set of unnatural sugar nucleotides could be accomplished by simply increasing enzyme concentration and incubation time.

Example 5

Engineering RmlA NTP-Specificity

Figure 3:
FIG. 3 illustrates the structural basis for engineering RmlA nucleotide-specificity. (A) Reaction catalyzed by the MobA guanylyltransferase. (B) Crystal structure of Escherichia coli MobA (45) with hydrogen bonding contacts between the nucleotide base and aspartate 71 highlighted. (C) Crystal structure of wt RmlA bound to UTP (9). The uracil base makes hydrogen bonding contacts with the glutamine 83 side chain of the enzyme. (D) Model of wild-type RmlA bound to GTP, showing the steric clash of the nucleotide base and Gln83. (E) Model of the RmlA Q83D mutant bound to GTP. In this model, steric infringements have been relieved and the side chain oxygens are appropriately positioned to hydrogen bond with the N1 nitrogen and the N2 exocyclic nitrogen of guanine. (F) Model of the RmlA Q83S mutant bound to ATP. In this model, the purine/glutamine steric clash has been relieved, and the serine hydroxyl may be able to form a hydrogen bond to the N1 of adenine.
Figure 3:
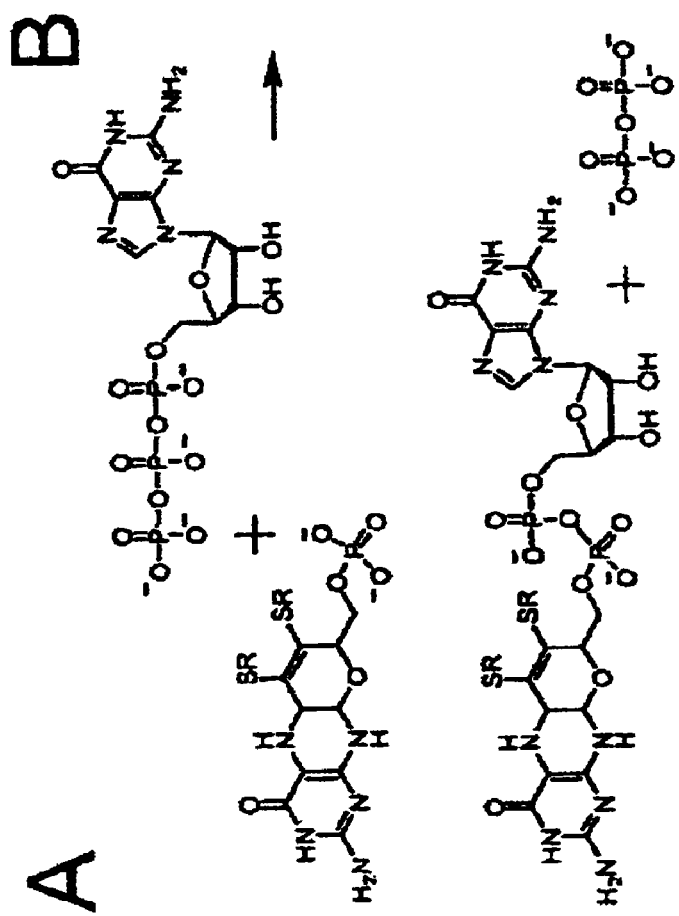
Figure 3:
Figure 3:
Figure 3:
Figure 3:

Examination of RmlA structural homologs emphasized that guanylyltransferases such as *E. coli* MobA—which catalyzes the phosphate-phosphate coupling reaction highlighted in FIG. 3A (Schwarz, G. (2005) Cell. Mol. Life Sci. 62, 2792-2810)—employ an aspartate to bind the GTP base pairing face (Lake et al. (2000) J. Biol. Chem. 275, 40211-40217). In RmlA, the structural equivalent of this moderately conserved MobA Asp71 (FIG. 3B) is RmlA Q83 (FIG. 3C), the side-chain of which hydrogen-bonds with the dTTP/UTP base-pairing face. The inventor identified this interaction, and the steric bulk of Gln83 (FIG. 3D), as contributing to the pyrimidine bias and, consequently, mutation of RmlA Gln83 would provide a novel avenue to engineering a 'universal' nucleotidyltransferase. Thus, Q83D (FIG. 3E) and the isosteric Q83N mutations were pursued. In addition, mutants that incorporated smaller non-polar (Q83A) or polar (Q83S, FIG. 3F) as well as larger isoelectronic substitutions (Q83E) at this position were also studied.

The activities of this mutant series, in the presence of alternative NTPs, was compared (Table 5, below) and the salient kinetic parameters for uniquely active mutants were subsequently determined (Table 4, see above).

TABLE 5

Relative activities of RmlA mutants[a,b]

|  | Q83E | Q83A | Q83S | Q83D | Q83N |
|---|---|---|---|---|---|
| ATP | 0.7 | 7.9 | 14.0 | 0.6 | 6.5 |
| CTP | 0.8 | 1.3 | 1.5 | 0.2 | 0.7 |
| GTP | 2.8 | 0.7 | 2.2 | 3.7 | 0.2 |
| dATP | 0.4 | 4.6 | 7.9 | 0.8 | 3.8 |
| dCTP | 1.1 | 0.8 | 1.4 | 1.2 | n.d.[c] |
| dGTP | 1.7 | 0.2 | 0.6 | 1.6 | 0.1 |
| UTP | 1.3 | 0.2 | 0.2 | 0.2 | 0.2 |
| dTTP | 1.0 | 0.2 | 0.3 | 0.2 | 0.3 |

[a] as compared to wt RmlA.
[b] with 10 mM Glucose-1-phosphate, 0.1-10 μM enzyme, 5 mM NTP, 10 mM MgCl$_2$, 10 U/mL inorganic pyrophosphatase, in 100 mM Tris-HCl pH 8.0 at 37° C.
[c] n.d.—not determined.

Consistent with the inventor's approach, changing glutamine to aspartic acid (Q83D) increased the guanine/thymidine bias (as measured by the ratio of specificity constants) by ~3 orders of magnitude, wherein this altered specificity derives in large part from a 6.5-fold improvement in apparent $K_M$ for GTP and a corresponding 21-fold increase in the dTTP $K_M$ (Table 4). In a similar manner, substituting glutamine for a smaller amino acid (Q83S) favored the adenine/thymidine bias by ~3 orders of magnitude, wherein dATP improvements were predominately apparent $K_M$-derived while ATP improvements were primarily apparent $k_{cat}$-dictated (Table 4). In this latter case, the effect of mutations on apparent $k_{cat}$ was not entirely expected, as reduction in steric overlap and the alteration of hydrogen bonds were anticipated to mainly influence substrate and product binding. No significant increase in (d)CTP turnover was observed in any of the mutants tested (Table 5).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All publications, patents and patent applications cited herein are hereby incorporated by reference in their entirety for all purposes.

What is claimed is:

1. An isolated mutant glucose-1-phosphate thymidylyltransferase (RmlA) nucleotidyltransferase consisting of the amino acid sequence of SEQ ID NO:1 except having a glutamic acid, alanine, serine, aspartic acid, or asparagine at position 83 of SEQ ID NO:1, wherein said isolated mutant RmlA nucleotidyltransferase exhibits an increased purine/pyrimidine bias in nucleoside triphosphate substrate specificity as compared to a corresponding non-mutated RmlA nucleotidyltransferase.

2. A method of providing a mutant RmlA nucleotidyltransferase with increased purine/pyrimidine bias in nucleoside triphosphate substrate specificity, comprising:
   (a) mutating an isolated nucleic acid sequence encoding an RmlA nucleotidyltransferase having the amino acid sequence set forth in SEQ ID NO:1 to replace glutamine at position 83 with glutamic acid, alanine, serine, aspartic acid, or asparagine;
   (b) expressing said isolated nucleic acid in a host cell; and
   (c) isolating from said host cell a mutant RmlA nucleotidyltransferase that exhibits an increased purine/pyrimidine bias in nucleoside triphosphate substrate specificity as compared to a corresponding non-mutated RmlA nucleotidyltransferase.

3. A method of providing a nucleotide-diphospho-sugar, comprising incubating a nucleoside triphosphate and a sugar-1-phosphate in the presence of an isolated mutant RmlA nucleotidyltransferase as set forth in claim 1 to enzymatically provide a nucleotide-diphospho-sugar.

4. The method according to claim 3, wherein said nucleoside triphosphate is a purine nucleoside triphosphate.

5. The method according to claim 3, wherein said nucleoside triphosphate is a pyrimidine nucleoside triphosphate.

6. The method according to claim 3, wherein said nucleoside triphosphate is a deoxyribose-containing nucleoside triphosphate.

7. The method according to claim 3, wherein said nucleoside triphosphate is a ribose-containing nucleoside triphosphate.

8. The method according to claim 3, wherein said sugar-1-phosphate is a hexose-1-phosphate.

9. The method according to claim 3, wherein said sugar-1-phosphate is 6-amino-6-deoxyglucose, glucosamine, mannose, galactose, glucose, N-acetyl-glucosamine, 3-O-methyl-glucose, 6-deoxyglucose, 3-azido-3-deoxyglucose, or 4-azido-4-deoxyglucose.

10. The method according to claim 3, wherein a plurality of different nucleoside triphosphates and a plurality of different sugar-1-phosphates are incubated in the presence of an isolated mutant RmlA nucleotidyltransferase as set forth in claim 1 to enzymatically synthesize a plurality of different nucleotide-diphospho-sugars.

* * * * *